United States Patent [19]

Bey et al.

[11] 4,221,914
[45] Sep. 9, 1980

[54] ALPHA-HALOMETHYL DERIVATIVES OF HISTAMINE AND RELATED COMPOUNDS

[75] Inventors: Philippe Bey, Strasbourg; Michel Jung, Illkirch Graffenstaden, both of France

[73] Assignee: Merrell Toraude et Compagnie, Strasbourg, France

[21] Appl. No.: 16,640

[22] Filed: Mar. 1, 1979

Related U.S. Application Data

[63] Continuation of Ser. No. 843,659, Oct. 19, 1977, abandoned.

[51] Int. Cl.² .................. C07D 233/64; C07D 233/66
[52] U.S. Cl. .................. 548/342; 424/273 R; 548/337
[58] Field of Search .............................. 548/337, 342

[56] References Cited

U.S. PATENT DOCUMENTS

| | | | |
|---|---|---|---|
| 3,169,971 | 2/1965 | Sletzinger et al. | 548/344 |
| 3,387,031 | 6/1968 | Johnson et al. | 548/344 |

FOREIGN PATENT DOCUMENTS

| | | | |
|---|---|---|---|
| 252872 | 10/1911 | Fed. Rep. of Germany | 548/342 |
| 715182 | 9/1954 | United Kingdom | 548/342 |

Primary Examiner—Richard Raymond
Attorney, Agent, or Firm—L. Ruth Hattan; Eugene O. Retter; George W. Rauchfuss, Jr.

[57] ABSTRACT

Novel halomethyl derivatives of amines of the following general structure

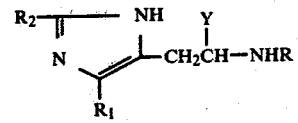

wherein Y is $FCH_2$—, $F_2CH$— or $F_3C$—; R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

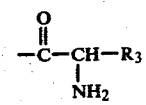

wherein $R_3$ is hydrogen, a straight or branched lower alkyl group of from 1 to 4 carbon atoms, benzyl or p-hydroxybenzyl; each of $R_1$ and $R_2$ is hydrogen, or a straight or branched lower alkyl group of from 1 to 4 carbon atoms and may be the same or different or $R_1$ is hydrogen and $R_2$ is fluorine; and pharmaceutically acceptable salts and individual optical isomers thereof.

10 Claims, No Drawings

ALPHA-HALOMETHYL DERIVATIVES OF HISTAMINE AND RELATED COMPOUNDS

This is a continuation of application Ser. No. 843,659, filed Oct. 19, 1977, now abandoned.

FIELD OF INVENTION

This invention relates to novel pharmaceutically useful halomethyl derivatives of histamine and related compounds.

BACKGROUND OF INVENTION

Most mammalian tissue contains histamine, concentration being particularly high in the skin, intestinal mucosa and the lungs. Every mammalian tissue that contains histamine, including white blood cells, appears capable of synthesizing the amine from histidine. The principal enzyme involved in catalyzing in vivo the conversion of histidine to histamine is histidine decarboxylase which is specific for the substrate L-histidine. In many tissues the chief storage site of histamine is the mast cell, or in the case of blood, the basophil which is the circulating counterpart of the fixed-tissue mast cell. Mast cells are not the only tissue source of histamine which is present in substantial amounts in the human epidermis, the central nervous system and the gastrointestinal mucosa.

Histamine is involved in various physiological processes. Histamine is released during the antigen-antibody reaction and is responsible, in large part, for the hypersensitivity reaction characterized by vasodilation, itching and edema formation. This type of antigen-antibody reaction wherein the principal cells involved are mast cells and basophils from which histamine is released is commonly referred to as an immediate hypersensitivity reaction. In addition to antigens, or allergens, histamine is released by many chemical substances, macromolecules, venoms, physical insult, such as heat and other injurious stimuli. Gastric acid secretion is known to be stimulated by histamine. Also, histamine is known to be frequently involved in initiation of sensory impulses evoking pain and itching. It has also been found that histamine levels are high in many tissues undergoing rapid growth, for example, embryonic tissue, regenerating liver and malignant growths.

Correlations between levels of histamine and histidine decarboxylase activity in tissues have been made. In the brain which contains histamine and histidine decarboxylase the turnover of histamine is rapid being augmented by stressful stimuli that also increases histidine decarboxylase activity. Inhibitors of L-histidine decarboxylase, such as α-hydrazinohistidine are known to lower histamine concentrations. In rat fetal tissue, wherein high levels of histamine are present, it has been shown that inhibition of L-histidine decarboxylase arrests fetal development.

The effects of histamine and its mode of action are well documented. It is believed that the amine exerts its effect through at least two receptors being classified as $H_1$ and $H_2$ receptors. Several agents are known to counter the effects of histamine, however, not all such agents prevent the formation of histamine. For example, classical antihistamines useful in treating allergic reactions are believed to exert their utility by interfering with the binding of histamine with $H_1$ receptors. Similarly agents useful in countering the stimulant effect of histamine on gastric acid secretion are believed to operate by interfering with the binding of histamine with $H_2$ receptors.

Agents capable of blocking $H_1$ receptors find use in treating acute exudative types of allergy, such as, seasonal rhinitis, hay fever, pollinosis relieving the sneezing, rhinorrhea, itching eyes, nose and throat. Such agents are also useful in controlling cough and to a degree find use in treating systemic anaphylaxis and bronchial asthma. Antihistamine agents which act through $H_1$ receptors are also useful in treating allergic dermatoses, such as acute and chronic urticaria, angioedema, itching pruritides, for example, atopic dermatitis and contact dermatitis, in the control of urticarial and edematous lesions of serum sickness, control of blood transfusion reactions and control of drug reactions attributable to allergic phenomena. Agents which block $H_2$ receptors are useful in treating peptic ulceration, the Zollinger-Ellison syndrome and other gastric hypersecretory states.

Agents which block the formation of histamine by inhibiting the activity of histidine decarboxylase, for example, α-methylhistidine and αhydrazinohistidine, are reported to be useful in the same manner as antihistaminic agents that are blockers of $H_1$ and $H_2$ receptors. Additionally histidine decarboxylase inhibitors are implicated as being useful in the control of certain tumors which are high in histamine content.

The compounds of the present invention prevent the formation of histamine by inhibiting the action of histidine decarboxylase rendering said compounds useful in treating pathophysiological conditions which result from histamine. The presently claimed compounds can be used in the same manner and for the same purposes as are compounds that antagnoize $H_1$ and $H_2$ receptors.

SUMMARY OF INVENTION

The compounds of the present invention are represented by the following general Formula I:

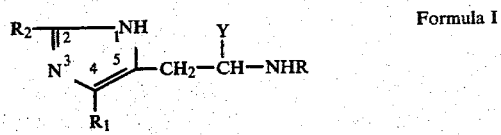

Formula I

In the above general Formula I Y is $FCH_2-$, $F_2CH-$, or $F_3C-$; R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

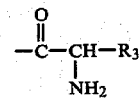

wherein $R_3$ is hydrogen, a straight or branched lower alkyl group of from 1 to 4 carbon atoms, benzyl or p-hydroxybenzyl; each of $R_1$ and $R_2$ is hydrogen, a straight or branched lower alkyl group of from 1 to 4 carbon atoms and may be the same or different or $R_1$ is hydrogen and $R_2$ is fluorine.

The pharmaceutically acceptable salts and individual optical isomers of the compounds of general Formula I are also included within the scope of this invention.

DETAILED DESCRIPTION OF INVENTION

Illustrative examples of straight chain or branched chain lower alkyl groups of from 1 to 4 carbon atoms in the above general Formula I are methyl, ethyl, n-propyl, isopropyl, n-butyl and tert-butyl.

As used in general Formula I the term alkylcarbonyl is taken to mean the group

wherein the alkyl group is straight or branched and has from 1 to 4 carbon atoms, for example, methyl, ethyl, n-propyl, isopropyl, n-butyl, and tert-butyl.

As used in general Formula I the term alkoxycarbonyl is taken to mean the group

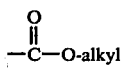

wherein the alkoxy group, that is, -O-alkyl has from 1 to 4 carbon atoms and is straight or branched, for example, methoxy, ethoxy, n-propoxy, isopropoxy, n-butoxy and tert-butoxy.

Illustrative examples of pharmaceutically acceptable salts of the compounds of this invention include nontoxic acid addition salts formed with inorganic acids, such as, hydrochloric, hydrobromic, sulfuric and phosphoric acid, and organic acids, such as, methane sulfonic, salicyclic, maleic, cyclamic, malonic, tartaric, citric and ascorbic acids. The salts are prepared by conventional means.

Preferred compounds of this invention are those of general Formula I wherein R is hydrogen or alkylcarbonyl wherein the alkyl moiety is straight or branched and has from 1 to 4 carbon atoms with compounds wherein R is hydrogen being more preferred. Another preferred embodiment of this invention is compounds of general Formula I wherein each of $R_1$ and $R_2$ is hydrogen or methyl. Compounds wherein $R_1$ is hydrogen and $R_2$ is fluorine are also preferred. More preferred compounds of this invention are those of general Formula I wherein Y is $FCH_2$— or $F_2CH$—.

Illustrative examples of compounds of the present invention are the following:

1-fluoromethyl-2-(5-imidazolyl)ethylamine,
1-fluoromethyl-2-[5-(2-fluoro)imidazolyl]ethylamine,
1-trifluoromethyl-2-[5-(4-methyl)imidazolyl]ethylamine,
1-fluoromethyl-2-[5-(2,4-dimethyl)imidazolyl]ethylamine,
1-difluoromethyl-2-[5-(2,4-diethyl)imidazolyl]ethylamine,
1-trifluoromethyl-2-[5-(2,4-diisopropyl)imidazolyl]ethylamine,
1-fluoromethyl-2-[5-(2,4-di-tert-butyl)imidazolyl]ethylamine,
1-difluoromethyl-2-[5-(2-n-butyl)imidazolyl]ethylamine,
N-[1-difluoromethyl-2-[5-(2-fluoro)imidazolyl]ethyl]acetamide,
N-[1-fluoromethyl-2-(5-imidazolyl)ethyl]methyl carbamate,
N-[1-fluoromethyl-2-[5-(2-ethyl)imidazolyl]ethyl]-2-aminopropionamide and
N-[1-difluoromethyl-2-(5-imidazolyl)ethyl]-2-amino-3-phenylpropionamide.

The compounds of Formula I are irreversible inhibitors of histidine decarboxylase, the enzyme which in vivo converts histidine to histamine. Thus the compounds block the formation of histamine which is known to play an important role in certain patho-physiological conditions. As inhibitors of histidine decarboxylase the compounds of the present invention are useful in the same manner as any known antihistiminic agent whether such agent exerts its effectiveness by blocking $H_1$ or $H_2$ receptors or other means. The compounds of this invention are useful in treating the patho-physiological conditions due to histamine. Thus, the compounds of general Formula I have many utilities being useful in treating acute exudative types of allergy, such as, seasonal rhinitis, hay fever, and pollinosis relieving the sneezing, rhinorrhea, itching eyes, nose and throat. The compounds of general Formula I are also useful in controlling cough and in treating systemic anaphylaxis and bronchial asthma, and are useful as broncholdilators. Also, the compounds of general Formula I are useful in treating allergic dermatoses, such as, acute urticaria, chronic urticaria, angioedema, itching pruritides, for example, atopic dermatitis and contact dermatitis. The compounds of general Formula I are also useful in treating urticarial and edematous lesions of serum sickness, blood transfusion reactions attributable to allergic phenomena and nausea. The compounds of general Formula I are also useful in treating peptic ulceration, the Zollinger-Ellison syndrome and other gastric hypersecretory states. As described hereinabove it has been found that histamine levels are high in rapidly growing tissues, such as, tumors, hence, the compounds of general Formula I by inhibiting the formation of histamine, may be useful in controlling the growth of certain tumors, for example, Walker mammary carcinoma and Erlich ascitic tumors.

The compounds of this invention can be administered in various manners to achieve the desired effect. The compounds can be administered alone or in the form of pharmaceutical preparations to the patient being treated either orally, parenterally, that is, subcutaneously, intravenously or intrperitoneally, or topically. The compounds can be administered by intranasal instillation or by application to mucous membranes such as that of the nose, throat and bronchial tubes, for example, in an aerosol spray containing small particles of a novel compound of this invention in a spray solution or dry powder form.

The amount of novel compound administered will vary and can be any effective amount. Depending on the patient, the condition being treated and the mode of administration, the quantity of novel compound administered may vary over a wide range to provide as an effective amount in a unit dosage form of from about 0.1 to 500 mg/kg (milligrams per kilogram) of body weight of the patient per dose and preferably from about 50 to 200 mg/kg to achieve the desired effect. For example, the desired effect can be obtained by consumption of a unit dosage form, such as, for example, a tablet containing from 10 to 500 mg of a novel compound of this invention taken 1 to 4 times daily.

As used herein the term patient is taken to mean warm blooded animals such as birds and mammals, for example, cats, dogs, rats, mice, guinea pigs, sheep, horses, bovine cows and humans.

The solid unit dosage forms can be of the conventional type. Thus, the solid form can be a capsule which can be of the ordinary gelatin type containing a novel compound of this invention and a carrier, for example, lubricant and inert fillers such as lactose, sucrose and corn starch. In another embodiment, the novel compounds are tableted with conventional tablet bases such as lactose, sucrose or cron starch in combination with binders such as acacia, corn starch or gelatin, disintegrating agents such as corn starch, potato starch, or alginic acid, and a lubricant such as stearic acid, or magnesium stearate.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable or synthetic origin, for example, peanut oil, soybean oil, and mineral oil. In general water, saline, aqueous dextrose, and related sugar solutions, ethanols and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

For use as aerosols the novel compounds in solution or suspension may be packaged in a pressurized aerosol container together with a gaseous or liquefied propellant, for example, dichlorodifluoromethane, dichlorodifluoromethane with dichlorodifluoroethane, carbon dioxide, nitrogen or propane, with the usual adjuvants such as cosolvents, and wetting agents, as may be necessary or desirable. The compounds may also be administered in a non-pressurized form such as in a nebulizer or atomizer.

The utility of the compunds of general Formula I as irreversible inhibitors of histidine decarboxylase may be demonstrated as follows. A compound of general Formula I is administered as an aqueous solution or suspension to rats or mice either orally or parenterally. At different time intervals after administration of the test compound the animals are injected intraperitoneally with 2 μCi of 2-$^{14}$C-L-histidine. Two hours after the labeled histidine injection the animals are sacrificed, and the amount of radioactive histamine present in the glandular part of the stomach is determined as described by K. M. Mole and D. M. Shepherd, J. Pharm. Pharmac. 25, 609–613 (1973).

In addition to being useful pharmacological agents, the compounds of this invention wherein R is hydrogen are useful as intermediates for the preparation of cephalosporin derivatives of the following general Formula II which are useful as antibiotics.

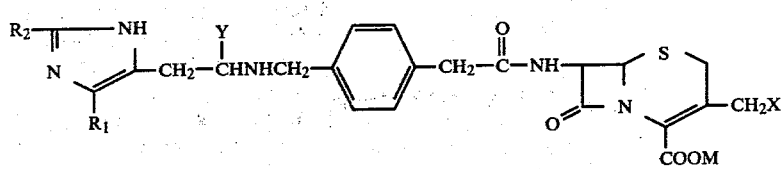

Formula II

In the above general Formula II X is hydrogen, acetoxy; M is hydrogen or a negative charge; $R_1$, $R_2$ and Y have the meanings defined in general Formula I.

The compounds of general Formula II and the pharmaceutically acceptable salts and individual optical isomers thereof are novel compounds useful as antibiotics and can be administered in a manner similar to that of many well known cephalosporin derivatives, for example, cephalexin, cephalothin, or cephaloglycine. The compounds of general Formula II and pharmaceutically acceptable salts and isomers thereof can be administered alone or in the form of pharmaceutical preparations either orally or parenterally and topically to warm blooded animals, that is, birds and mammals, for example, cats, dogs, bovine cows, sheep, horses and humans. For oral administration the compounds can be administered in the form of tablets, capsules or pills or in the form of elixirs or suspensions. For parenteral administration, the compounds may best be used in the form of a sterile aqueous solution which may contain other solutes, for example, enough saline or glucose to make the solution isotonic. For topical administration the compounds of general Formula II, salts and isomers thereof may be incorporated into creams or ointments.

Illustrative examples of bacteria against which the compounds of general Formula II and the pharmaceutically acceptable salts and individual optical isomers thereof are active are *Staphylococcus aureus, Salmonella schotmuehleri, Klebsiella pneumoniae, Diplococcus pneumoniae* and *Streptococcus pyogenes*.

Illustrative pharmaceutically acceptable non-toxic inorganic acid addition salts of the compounds of general Formula II are mineral acid addition salts, for example, hydrogen chloride, hydrogen bromide, sulfates, sulfamates, phosphate, and organic acid addition salts are, for example, maleate, acetate, citrate, oxalate, succinate, benzoate, tartrate, fumarate, malate and ascorbate. The salts can be formed by conventional means.

Illustrative examples of cephalosporin derivatives as represented by general Formula II are 7-[[2-[4-[1-fluoromethyl-2-(4-imidazolyl)ethylaminomethyl]-phenyl]acetyl]amino]-3-acetyloxymethyl-8-oxo-5-thia-1-azabicyclo[4.2.0]oct-2-ene-2-carboxylic acid, 7-[[2-[4-[1-difluoromethyl-2-[5-(2-fluoro)imidazolyl]ethylaminomethyl]phenyl]acetyl]amino]-3-acetyloxymethyl-8-oxo-5-thia-1-azabicyclo[4.2.0]oct-2-ene-2-carboxylic acid and 7-[[2-[4-[1-fluoromethyl-2-[4-(2,5-dimethyl)imidazolyl]ethylaminomethyl]phenyl]acetyl]amino]-3-acetyloxymethyl-8-oxo-5-thia-1-azabicyclo[4.2.0]oct-2-ene-2-carboxylic acid.

The compounds of general Formula II are prepared by reacting a compound of the formula

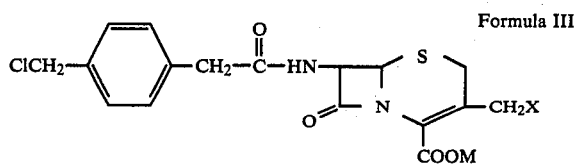

Formula III wherein X and M have the meanings defined in general Formula II, which compounds are prepared as described in U.S. Pat. No. 3,919,206 which patent is incorporated herein by reference thereto, with a compound of general Formula I wherein R is hydrogen. The reaction is generally carried out in a solvent, such as, a lower alcohol, for example, methanol, ethanol or isopropyl alcohol, or dimethylsulfoxide, dimethylformamide or aqueous mixtures of these solvents. The temperature of the reaction may vary from about 0° to 125° C. and the reaction time may vary from about ½ hour to 24 hours. Following the solvolysis reaction the amino protecting group is removed by acid hydrolysis, and the cephalosporin products are isolated by conventional procedures.

The compounds of general Formula I wherein R is hydrogen are prepared by reducing an appropriately substituted 5-imidazolyl halomethyl ketone derivative, as described by Formula IV below, to the corresponding alcohol which is treated with one equivalent of an imide, such as, phthalimide, succinimide or maleimide, 1.1 equivalents of a phosphine, for example, triphenylphosphine or a trialkylphosphine, such as, tri-n-butylphosphine and 1.1 equivalents of diethyl azodicarboxylate in a solvent, such as, ethers, for example, diethyl ether, tetrahydrofuran or p-dioxane, benzene or dimethoxyethane at about 0° to 100° C., preferably about 25° C. for about ½ hour to 24 hours under an inert atmosphere, for example, nitrogen or argon and hydrolyzing the thus obtained imido derivative to the free amine.

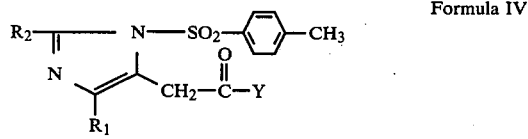

Formula IV

In the above general Formula IV Y, $R_1$ and $R_2$ have the meanings defined in general Formula I.

Reduction of the ketones of Formula IV to the corresponding alcohol is achieved chemically using, for example, 1 to 10 equivalents of a metal hydride reducing reagent, such as lithium borohydride, sodium borohydride, sodium cyanoborohydride, or lithium aluminum hydride, borane or dimethylthioborane or catalytically using, for example, Raney nickel, rhodium, palladium on charcoal, or platinum oxide. Overall the reaction time varies from about 10 minutes to 24 hours and the temperature varies from about −40° C. to 100° C. depending on the reducing reagent employed. When chemical reduction is employed the reaction time generally varies from about 10 minutes to 24 hours with temperatures varying from about −40° C. to 65° C. Suitable solvents for chemical reduction of compounds of general Formula IV include lower alcohols, such as, methanol or ethanol or ethers, such as, diethyl ether or tetrahydrofuran. When catalytic reduction is employed the reaction time varies from about 1 hour to 24 hours, the reaction temperature varies from about 25° to 100° C. and the pressure varies from 1 to 120 atmospheres. Suitable solvents for catalytic reduction of compounds of general Formula IV include lower alcohols, for example, methanol or ethanol, acetic acid, or ethyl acetate. Chemical reduction is preferred.

Hydrolysis to the amine and to remove any ring protecting groups is achieved using a strong mineral acid, for example, hydrochloric acid, hydrobromic acid or sulfuric acid or an organic acid, for example, toluene sulfonic acid or trifluoroacetic acid in water at reflux temperature for about 4 to 48 hours, or using, for example, 1 to 3 equivalents of hydrazine, methylhydrazine or methylamine at a temperature of from about 25° C. to reflux for about 1 to 12 hours followed by treatment with a strong mineral acid or organic acid as described above or by hydrogenolysis of the protecting group when appropriate.

As indicated above tri-alkylphosphines, such as, tri-n-butylphosphine may be employed in the reaction. The term alkyl is taken to mean an alkyl group having from 1 to 10 carbon atoms. The tri-alkylphosphines are known in the art or may be obtained by procedures known in the art.

The compounds of general Formula I wherein R is alkylcarbonyl wherein the alkyl moiety is straight or branched and has from 1 to 4 carbon atoms are prepared by treating the corresponding derivatives wherein R is hydrogen with an acid halide of the formula

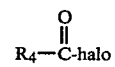

wherein halo is a halogen atom, for example, chlorine or bromine and $R_4$ is a straight or branched alkyl group having from 1 to 4 carbon atoms in water in the presence of a base such as sodium hydroxide or sodium borate at a temperature of from 0° C. to 25° C. for from ½ hour to 6 hours.

The compounds of general Formula I wherein R is alkoxycarbonyl wherein the alkoxy moiety is straight or branched and has from 1 to 4 carbon atoms are prepared by treating the corresponding derivative wherein R is hydrogen with an alkyl haloformate of the formula

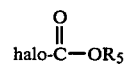

wherein halo is a halogen atom such as chlorine or bromine and $R_5$ is a straight or branched alkyl group having from 1 to 4 carbon atoms in water in the presence of a base such as sodium hydroxide or sodium borate at a temperature of from about 0° C. to 25° C. for from about ½ hour to 6 hours.

The compounds of general Formula I wherein R is

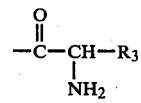

wherein $R_3$ is hydrogen, a straight or branched lower alkyl group of from 1 to 4 carbon atoms, benzyl or p-hydroxybenzyl are prepared by treating the corresponding derivative wherein R is hydrogen with an acid of the formula

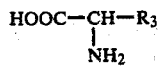

or an anhydride thereof wherein R₃ has the meaning defined above and the amino group is suitably protected with, for example, tertiary butoxycarbonyl or benzyloxycarbonyl in a solvent such as, tetrahydrofuran, dioxane or other ethers or methylene chloride or chloroform and in the presence of a dehydrating agent when the free acid is employed at a temperature of about 0° to 35° C. for about 1 to 12 hours followed by acid and base hydrolysis to remove the protecting group.

Compounds of general Formula IV wherein Y is FCH₂— are prepared by treating an appropriately substituted 5-imidazolylmethyl substituted methyl ketone of the formula Formula V

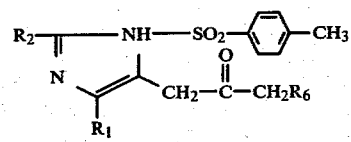

wherein R₁ and R₂ have the meanings defined in Formula I and R₆ is a suitable leaving group, such as, halogen, for example, chlorine, bromine, or iodine, mesylate, tosylate, triflate or trifluoroacetate with an appropriate fluorinating reagent, such as, potassium fluoride, silver fluoride, cesium fluoride, thallium fluoride or tetra-butylammonium fluoride in a suitable solvent, such as, dimethoxyethane, dimethylsulfoxide, dimethylformamide, ethylene glycol, acetonitrile, acetone, benzene or hydrogen fluoride at a temperature of from about 0° to 200° C. for about 2 to 48 hours. The leaving group R₆ in Formula V may also be a diazo group in which case the fluorinating reagent employed is hydrogen fluoride/pyridine. Suitable solvents for the reaction wherein R₆ is a diazo group are aprotic solvents, such as, diethyl ether, tetrahydrofuran and pentane, and the reaction time varies from about 30 minutes to 24 hours at a temperature of about −20° to 65° C. Illustratively, a suitable diazo ketone derivative, that is, a compound of Formula V wherein R₆ is a diazo group in a suitable aprotic solvent is added to a solution of hydrogen fluoride/pyridine cooled to −10° C. The reaction mixture is stirred vigorously at −10° C. for 1 hour then at about 25° C. for 2 hours then poured on ice. The organic phase is separated, washed with base, for example, sodium bicarbonate, dried over magnesium sulfate and concentrated under vacuum to afford an appropriately substituted 5-imidazolylmethyl fluoromethyl ketone derivative of Formula IV.

The diazo ketone derivatives, that is, the compounds of Formula V wherein R₆ is a diazo group, are obtained from the corresponding acid halide, that is, an appropriately substituted 2-(5-imidazolyl)acetyl halide wherein halide may be, for example, chloride by slowly adding said acid halide in an aprotic solvent, such as, diethyl ether, tetrahydrofuran, pentane, hexane, benzene, dimethoxyethane or dioxane to a solution of diazomethane cooled to about −40° to 20° C. in ether followed by vigorous stirring at about 25° C. for about 1 to 24 hours. The thus obtained diazo ketone derivative can be isolated by standard procedures, for example, evaporation of the solvent with purification by recrystallization or chromatography or can be treated without isolation with an appropriate fluorinating reagent as described above.

The appropriately substituted diazo ketone derivative described above can also be used to prepare compounds of Formula V wherein R₆ is, for example, halogen, mesylate, tosylate, triflate or trifluoroacetate by procedures generally known in the art. To obtain compounds of general Formula V wherein R₆ is halogen, such as, chlorine, bromine, or iodine the corresponding compound of Formula V wherein R₆ is a diazo group in a suitable aprotic solvent is treated respectively with aqueous hydrogen chloride, hydrogen bromide or hydrogen iodide. To obtain compounds of Formula V wherein R₆ is mesylate, tosylate, triflate or trifluoroacetate the corresponding diazo ketone derivative, that is, an appropriate compound of Formula V wherein R₆ is a diazo group in a suitable aprotic solvent is treated with dilute sulfuric acid to give the corresponding 5-imidazolylmethyl methanol ketone derivative which is esterified with an appropriate acid chloride or acid anhydride of methane sulfonic acid, p-toluene sulfonic acid, trifluoromethyl sulfonic acid or trifluoroacetic acid.

The appropriately substituted 2-(5-imidazolyl)acetyl halide used to prepare the diazo ketone derivatives of Formula V, that is, compounds wherein R₆ is a diazo group are obtained from the corresponding acids, for example, by treatment with thionyl chloride in an aprotic solvent, such as, diethyl ether, tetrahydrofuran, benzene or dichloromethane at a temperature ranging from about 0° C. to the reflux temperature of the solvent for about 1 to 24 hours. Alternatively, 1 equivalent of the corresponding acid may be treated with 1 equivalent of oxalyl chloride in an aprotic solvent as illustrated above at a temperature of about 0° to 40° C. for about 1 to 24 hours. The appropriately substituted 2-(5-imidazolyl)acetic acid derivatives employed as described above are obtained by treating the appropriate acid with p-toluenesulfonyl halide, for example, p-toluenesulfonyl chloride in the presence of a base at about 25° C. for about 4 to 20 hours. The appropriate acids are known in the art or may be obtained by acid or base hydrolysis of an appropriately substituted 5-imidazolylacetonitrile by procedures well known in the art. The appropriately substituted 5-imidazolylacetonitriles are known in the art or may be prepared by treating the corresponding 5-imidazolylmethyl halide, for example, chloride, with potassium cyanide or sodium cyanide in a protic solvent, such as, ethanol, dimethoxyethane, water or glycol or an aprotic solvent such as diethylether, benzene, hexamethylphosphortriamide, dimethylsulfoxide, dimethylformamide, acetamide or dimethylacetamide for about 1 to 48 hours at a temperature of about 0° to 150° C. The appropriately substituted 5-imidazolylmethyl halides are known in the art or may be prepared by procedures well known in the art from the corresponding appropriately substituted 5-imidazolylmethanol derivatives which are known in the art, for example, by treatment of the appropriate methanol with halogen acids, such as, hydrogen bromide, hydrogen iodide or hydrogen chloride or by treatment with thionyl chloride, phosphorus pentachloride, phosphorus trichloride or phosphorus oxychloride.

Compounds of general Formula IV wherein Y is F₂CH— are obtained by treating [[(methylsulfinyl)methyl]thio]methane or [[(ethylsulfinyl)methyl]thio]ethane with a suitable strong base followed by alkylation with an appropriately substituted 5-imidazolylmethyl derivative of the formula

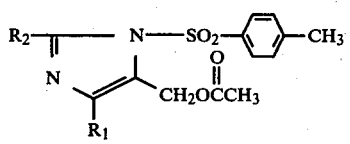

Formula VI wherein $R_1$ and $R_2$ have the meanings defined in Formula IV, treating the thus formed appropriately substituted 5-imidazolylmethyl substituted sulfinyl derivative with a suitable strong base followed by alkylation with a suitable halomethylhalo alkylating reagent selected from chlorodifluoromethane, bromodifluoromethane, and difluoromethane followed by hydrolysis with aqueous acid to give the appropriately $R_1$, $R_2$ substituted 5-acetoxymethylimidazole derivative which is treated with a p-toluenesulfonyl halide, for example, p-toluenesulfonyl chloride in the presence of a base, such as sodium carbonate or an organic amine at about 25° C. for about 4 to 20 hours.

Suitable strong bases which may be employed in preparing the difluoromethyl substituted ketone derivatives as described above are illustratively, sodium hydride, dilithium acetylide, lithium diisopropylamide, butyl lithium, potassium tert-butoxide, sodium tert-butoxide, lithium tert-butoxide, phenyl lithium, methyl lithium, sodium amide, lithium amide or potassium hydride.

The alkylation reactions described in preparing the difluoromethyl ketone derivatives are carried out in a suitable solvent, such as, tetrahydrofuran, diethyl ether, hexamethylphosphortriamide, dimethylsulfoxide, or benzene at a temperature ranging from about −78° to 65° C. for about 30 minutes to 24 hours. A preferred temperature for the difluoromethyl alkylation step is about 40° C. The alkylated sulfinyl intermediates are isolated by quenching with brine followed by extraction with, for example, diethyl ether, dichloromethane, or benzene.

Hydrolysis of the alkylated sulfinyl derivatives to the ketone is achieved using aqueous mineral acid, such as, hydrochloric, hydrobromic, perchloric or sulfuric in a solvent such as tetrahydrofuran, acetonitrile, diethyl ether or benzene at about −20° to 105° C., preferably about 2 hours. Generally, 0.3 equivalents of mineral acid in 1.5% water is employed. The specific examples contained herein further illustrate the preparation of the difluoromethyl ketone derivatives of Formula IV.

The compounds of Formula VI are prepared by treating the appropriately substituted imidazol-5-ylmethanol derivatives of the formula

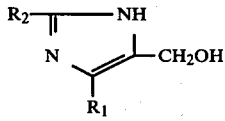

Formula VII wherein $R_1$ and $R_2$ are as defined in Formula VI with a p-toluenesulfonyl halide, for example, p-toluenesulfonyl chloride in the presence of a base at about 25° C. for about 4 to 20 hours to give the corresponding 1-tosylimidazol-5-ylmethanol whith is treated with acetic anhydride in the presence of an organic base, such as triethylamine for about 2 to 6 hours at about 25° C.

The compounds of general Formula IV wherein Y is $F_3C-$ are prepared by treating a compound of Formula VI with triphenylphosphine in a solvent, such as, hydrocarbons, for example, benzene or toluene or lower alcohols, such as, methanol or ethanol, or acetonitrile, tetrahydrofuran, diethyl ether, or dimethoxyethane at about 25° C. to the reflux temperature of the solvent for about 10 minutes to 96 hours. On cooling a precipitate forms which is washed with solvent and recrystallized using, for example, ethylacetate, acetonitrile or a lower alcohol to give the appropriately substituted 5-imidazolylmethyl phosphonium salt. The appropriately substituted 5-imidazolylmethyl phosphonium salt may also be obtained by treating an appropriately substituted 5-imidazolylmethanol with a triphenylphosphonium salt, such as, triphenylphosphonium bromide using generally the same reaction conditions set forth above. The appropriately substituted 5-imidazolylmethyl triphenylphosphonium salt is added to excess (up to 25%) sodium or lithium metal dissolved in liquid ammonia to which is added a catalytic amount of ferric nitrate with stirring for about 10 minutes to 3 hours after which the ammonia is evaporated under an inert atmosphere, such as, nitrogen or argon. An appropriate solvent, such as, benzene, toluene, diethyl ether, tetrahydrofuran or dimethoxyethane is added and the resulting 5-imidazolylmethylidenephosphorane is collected. The 5-imidazolylmethylidenephosphorane is treated with an ester, such as, a lower alkyl, for example, methyl, ethyl, n-propyl, isopropyl or n-butyl ester of trifluoroacetic acid in a solvent such as benzene, toluene, diethyl ether, tetrahydrofuran or dimethoxyethane under an inert atmosphere such as nitrogen or argon at a temperature of about 0° C. to the reflux temperature of the solvent for about 30 minutes to 24 hours after which the reaction mixture is concentrated and distilled to give the olefin which is treated with aqueous mineral acid, such as hydrochloric or hydrobromic acid or an organic acid such as trifluoroacetic acid or p-toluene sulfonic acid using a cosolvent such as tetrahydrofuran, diethyl ether, or benzene for about 30 minutes to 24 hours at a temperature of from about 0° C. to the reflux temperature of the solvent. The amount of acid employed may vary from a catalytic amount to concentrated acid. The chemistry employed in preparation of the compounds of Formula IV wherein Y is $F_3C-$ as set forth hereinabove is generally described by P. H. Betmann, Ang. Chem. Int. Ed. 1966, p. 308.

The following examples further illustrate the invention.

EXAMPLE 1

7-((4-(1-Difluoromethyl-2-(5-imidazolyl)ethyl-)aminomethyl)phenyl)acetylamino)-3-acetyloxymethyl-8-oxo-5-thia-1-azabicyclo[4.2.0]oct-2-ene-2-carboxylic acid A mixture of 1 g of 3-acetyloxymethyl-7-[[2-[4-(chloromethyl)phenyl]acetyl]amino]-8-oxo-5-thia-1-azabicyclo[4.2.0]oct-2-ene-2-carboxylic acid and 1 g of 1-fluoromethyl-2-(5-imidazolyl)ethylamine in 50 ml of ethanol is stirred at 25° C. for 24 hours after which the solvent is removed leaving a residue which is chromatographed on silica gel using benzene-acetone as the eluant to give the title compound.

EXAMPLE 2

An illustrative composition for hard gelatin capsules is as follows:

| | |
|---|---|
| (a) 1-difluoromethyl-2-(5-imidazolyl)-ethylamine | 20 mg |
| (b) talc | 5 mg |
| (c) lactose | 90 mg |

The formulation is prepared by passing the dry powders of (a) and (b) through a fine mesh screen and mixing them well. The powder is then filled into hard gelatin capsules at a net fill of 115 mg per capsule.

EXAMPLE 3

An illustrative composition for tablets is as follows:

| | |
|---|---|
| (a) 1-fluoromethyl-2-(5-imidazolyl)-ethylamine | 20 mg |
| (b) starch | 43 mg |
| (c) lactose | 45 mg |
| (d) magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 4

An illustrative composition for an injectable suspension is the following 1 ml ampul for an intramuscular injection.

| | Weight per cent |
|---|---|
| (a) 1-difluoromethyl-2-(5-imidazolyl)-ethylamine | 1.0 |
| (b) polyvinylpyrrolidone | 0.5 |
| (c) lecithin | 0.25 |
| (d) water for injection to make | 100.0 |

The materials (a)–(d) are mixed, homogenized, and filled into 1 ml ampuls which are sealed and autoclaved 20 minutes at 121° C. Each ampul contains 10 mg per ml of novel compound (a).

EXAMPLE 5

1-Fluoromethyl-2-(5-imidazolyl)ethylamine hydrobromide (A) To a solution of 29 mmole of diazomethane in 84 ml of ether cooled to 0° C. and magnetically stirred is added dropwise over 45 minutes a solution of 4.32 g (14.5 mmole) of 1-tosyl-5-imidazolylacetyl chloride in 60 ml of ether. After stirring for 1½ hours at 25° C. the reaction mixture is added to a solution of hydrogen chloride/pyridine precooled to 0° C. The resulting heterogeneous solution is stirred at 25° C. for 1½ hours then poured onto ice (150 g). The organic phase is separated, washed with sodium bicarbonate (pH of 8) then with brine and dried over magnesium sulfate. Concentration of the mixture under reduced pressure yields 1-tosyl-5-imidazolylmethyl fluoromethyl ketone.

(B) A solution of 20 mmole of 1-tosyl-5-imidazolyl-methyl fluoromethyl ketone in 25 ml of methanol cooled to −10° C. is treated with 30 mg of sodium borohydride. After two hours at from −10° to 0° C. the reaction mixture is neutralized with 6 M HCl and concentrated under vacuo. The residue is extracted several times with chloroform. Evaporation of the solvent affords an oil which is purified by distillation under high vacuum to give 3-fluoro-1-(1-tosyl-5-imidazolyl)propan-2-ol. A solution of 2 g of 3-fluoro-1-(1-tosyl-5-imidazolyl)propan-2-ol, 1.37 g of phthalimide, 1.74 g of diethylazodicarboxylate in 2.4 g of triphenylphosphine and 25 ml of tetrahydrofuran is stirred under nitrogen at 25° C. for 20 hours after which the solvent is evaporated at reduced pressure and the residue is taken up in benzene. The insoluble material is discarded and the semi-solid residue obtained after concentration of the filtrate under vacuum is recrystallized using dichloromethane/diethylether to give the fluorophthalimide derivative. A solution of 1.12 g of the fluorophthalimide derivative in 0.18 g of hydrazine hydrate in 42 ml of absolute ethanol is heated at reflux for 5 hours. Upon cooling the solution is concentrated under vacuum to a volume of 15 ml, allowed to stand overnight at 0° C. then filtered. The filtrate is concentrated and distilled under high vacuum to afford 1-fluoromethyl-2-(1-tosyl-5-imidazolyl)ethylamine which is combined with 6 ml of 47% hydrogen bromide and heated under nitrogen at 100° C. for 4 hours then concentrated under reduced pressure to give a solid residue. The residue is recrystallized from ethanol-diethylether to give 1-fluoromethyl-2-(5-imidazolyl)ethylamine hydrobromide.

EXAMPLE 6

5-Acetoxymethyl-1-tosylimidazole (A) To an ice cold solution of 0.08 mole of sodium bicarbonate in 40 ml of water is added 0.02 mole of imidazol-5-ylmethanol hydrochloride followed by a solution of 0.025 mole of tosylchloride in 30 ml of ethyl acetate. The reaction mixture is stirred at room temperature for 5 hours. The organic phase is separated, washed with sodium bicarbonate, and dried over magnesium sulfate and concentrated under reduced pressure. The residue is crystallized from ethyl acetate to afford 1-tosylimidazol-5-ylmethanol.

(B) To a solution of 10 mmole of 1-tosylimidazol-5-ylmethanol in 10 ml of chloroform is added dropwise 20 mmole of triethylamine followed by the addition of 13 mmole of acetic anhydride over a period of 2 hours. Stirring is continued for 5 hours at 25° C. after which the solvent is removed under reduced pressure. The residue is partitioned between ethyl acetate and water. The organic phase is washed with sodium bicarbonate, dried over magnesium sulfate and evaporated under vacuo. Recrystallization of the residue from ethyl acetate yields 5-acetoxymethyl-1-tosylimidazole.

EXAMPLE 7

Difluoromethyl 1-tosylimidazol-5-ylmethyl ketone (A) A solution of 10 mmole of [[(ethylsulfinyl)methyl]thio]ethane in 20 ml of dry tetrahydrofuran is heated at 0° C. with 10 mmole of lithium diisopropylamide, prepared from a solution of diisopropylamine M in tetrahydrofuran and butyllithium 2 M in hexane. After 30 minutes at 0° C. a solution of 12 mmole of 5-acetyloxymethyl-1-tosylimidazole in 10 ml of tetrahydrofuran is added. The reaction mixture is stirred at 25° C. overnight then is quenched with brine and extracted with ether. The organic phase is washed with brine, dried over magnesium sulfate and concentrated under reduced pressure to give [[(ethylsulfinyl)-1-tosylimidazol-5-ylmethyl]thio]ethane. To a solution of 20 mmole of [[(ethylsulfinyl)-1-tosylimidazol-5-ylmethyl]thio]ethane in 20 ml of dry tetrahydrofuran is added at 0° C. and under nitrogen a solution of 20 mmole of lithium diisopropylamide prepared from a solution of diisopropylamine M in tetrahydrofuran and butyl lithium 2 M in hexane. Stirring is continued for 30 minutes at 25° C. after which a stream of chlorodifluoromethane is bubbled into the reaction mixture for ½ hour. The reaction mixture is maintained at 40° C. for 3 hours then quenched with brine and extracted with ether. The organic phase is separated, washed with brine, dried over magnesium sulfate and concentrated under reduced pressure to afford [[(ethylsulfinyl)((difluoromethyl)-1-tosylimidazol-5-ylmethyl)]thio]ethane. To a solution of 30 ml of [[(ethylsulfinyl)((difluoromethyl)-1-tosylimidazol-5-ylmethyl)]thio]ethane in 33 ml of acetonitrile is added at 0° C. a 70% aqueous solution of perchloric acid (1.1 ml). After stirring for 2 hours at 0° C. the reaction mixture is poured into 60 ml of water then extracted with difluoromethane. The organic phase is washed with sodium bicarbonate then water, dried over magnesium sulfate and concentrated under reduced pressure to afford difluoromethyl 5-imidazolylmethyl ketone.

(B) When in the procedure of Example 6 (A) an appropriate amount of difluoromethyl 5-imidazolylmethyl ketone hydrochloride, prepared from the free base obtained above, is substituted for imidazol-5-ylmethanol hydrochloride, and an appropriate amount of triethylamine is substituted for sodium bicarbonate, difluoromethyl 1-tosylimidazol-5-ylmethyl ketone is obtained.

EXAMPLE 8

Trifluoromethyl 1-tosylimidazol-5-ylmethyl ketone

A mixture of 20 mmole of 5-acetoxymethyl-1-tosylimidazole and 22 mmole of triphenylphosphine in 100 ml of benzene is heated at reflux temperature for 4 days. The solid which separates on cooling is filtered, washed with benzene, dried under reduced pressure then added slowly to a solution of 20 mmole of sodium amide in 100 ml of liquid ammonia (prepared by adding 0.46 g of sodium to liquid ammonia in the presence of a catalytic amount of ferric nitrate). After stirring for 10 minutes the ammonia is evaporated under a stream of nitrogen. To the residue is added 100 ml of anhydrous benzene and the heterogeneous mixture is heated at reflux for 10 minutes. The solid residue is filtered, and to the filtrate containing salt-free 1-tosyl-5-imidazolylmethylidene triphenylphosphorane is added 5.10$^{-2}$ M of ethyl trifluoroacetate. The reaction mixture is heated at reflux temperature under nitrogen for 12 hours. Concentration of the solvent leaves a residue which is distilled under high vacuum to afford 2-ethoxy-1,1,1-trifluoro-3-(1-tosyl-5-imidazolyl)prop-2-ene. A solution of 3 g of 2-ethoxy-1,1,1-trifluoro-3-(1-tosyl-5-imidazolyl)-prop-2-ene in 50 ml of ether is treated with a solution of 1 M of sulfuric acid in 50 ml of water. The reaction mixture is stirred for ½ hour at 25° C. The ether phase is separated, washed with brine, dried over magnesium sulfate and concentrated to give trifluoromethyl 1-tosylimidazol-5-ylmethyl ketone.

EXAMPLE 9

2-Isopropyl-1-tosylimidazol-5-ylmethyl fluoromethyl ketone

To 200 ml of cold thionyl chloride is added 0.1 mole of 3-isopropylimidazol-5-ylmethanol. After stirring for 1 hour at 25° C. the excess thionyl chloride is evaporated under reduced pressure to give crude 5-chloromethyl-2-isopropylimidazole hydrochloride. To an ice cold solution of 5 mmole of 5-chloromethyl-2-isopropylimidazole hydrochloride in 25 ml of dry dimethylformamide is added a cold solution of powdered sodium cyanide (18 mmole) in 30 ml of dimethylformamide. The mixture is stirred overnight at 25° C. then diluted with 200 ml of water and neutralized with sodium bicarbonate. The solution is saturated with sodium chloride and extracted with ethylacetate (5×50 ml). The organic extracts are washed with water, dried over magnesium sulfate and evaporated under reduced pressure to give a solid residue which is sublimed to give 5-cyanomethyl-2-isopropylimidazole. 5-cyanomethyl-2-isopropylimidazole (10 mmole) is heated with 10 ml of concentrated hydrochloric acid for 12 hours at reflux temperature then concentrated under reduced pressure to give 2-isopropylimidazol-5-ylacetic acid hydrochloride. To an ice cold solution of 0.08 mole of sodium carbonate in 40 ml of water is added 2-isopropylimidazol-5-ylacetic acid hydrochloride followed by 0.025 mole of tosyl chloride dissolved in 30 ml of ethyl acetate. After stirring for 5 hours at 25° C. the reaction mixture is neutralized with hydrochloric acid M and extracted with ethyl acetate. The organic phase is washed with water, dried over magnesium sulfate and concentrated under reduced pressure to yield 2-isopropyl-1-tosylimidazol-5-ylacetic acid. To a suspension of the sodium salt of 2-isopropyl-1-tosylimidazol-5-ylacetic acid in 100 ml of benzene is added 1 equivalent of oxalyl chloride. The reaction mixture is stirred at 25° C. for 12 hours. The precipitate is filtered off and the filtrate concentrated under reduced pressure to give 2-isopropyl-1-tosylimidazol-5-ylacetyl chloride. To a solution of 29 mmole of diazomethane in 84 ml of ether cooled to 0° C. and magnetically stirred is added dropwise over 45 minutes a solution of 14.3 mmole of 2-isopropyl-1-tosylimidazol-5-ylacetyl chloride in 60 ml of ether. After stirring for 1½ hours at 25° C. the reaction mixture is added to a solution of hydrogen fluoride/pyridine precooled to 0° C. The resulting heterogeneous solution is stirred at 25° C. for 1½ hours then poured onto 150 g of ice. The organic phase is separated, washed with sodium bicarbonate (pH of 8) then with brine and dried over magnesium sulfate. Concentration of the mixture under reduced pressure yields 2-isopropyl-1-tosylimidazol-5-ylmethyl fluoromethyl ketone.

EXAMPLE 10

When in the procedure of Example 6 an appropriate amount of 2-fluoroimidazol-5-ylmethanol, 2,4-dimethylimidazol-5-ylmethanol, 2,4-isopropylimidazol-5-ylmethanol, 2-isopropyl-5-ethylimidazol-5-ylmethanol, or 2-fluoroimidazol-5-ylmethanol is substituted for imidazol-5-ylmethanol the following respective compounds are obtained:
5-acetoxymethyl-2-fluoro-1-tosylimidazole,
5-acetoxymethyl-2,4-dimethyl-1-tosylimidazole,
5-acetoxymethyl-2,4-diisopropyl-1-tosylimidazole, 5-acetoxymethyl-2-isopropyl-1-tosylimidazole, and
5-acetoxymethyl-2-fluoro-1-tosylimidazole.

EXAMPLE 11

When in the procedure of Example 7 (A) an appropriate amount of the imidazole compounds obtained in Example 10 is substituted for 5-acetoxymethyl-1-tosylimidazole the following respective ketone compounds are obtained:
2-fluoroimidazol-5-ylmethyl difluoromethyl ketone,
difluoromethyl 2,4-dimethylimidazol-5-ylmethyl ketone,
difluoromethyl 2,4-diisopropylimidazol-5-ylmethyl ketone,
difluoromethyl 2-isopropylimidazol-5-ylmethyl ketone, and
2-fluoroimidazol-5-ylmethyl difluoromethyl ketone.

EXAMPLE 12

When in the procedure of Example 6 (A) an appropriate amount of the hydrochloride salt of the ketone compounds obtained in Example 11 is substituted for imidazol-5-ylmethanol the following respective compounds are obtained:
2-fluoro-1-tosylimidazol-5-ylmethyl difluoromethyl ketone,
difluoromethyl 2,4-dimethyl-1-tosylimidazol-5-ylmethyl ketone,
difluoromethyl 2,4-diisopropyl-1-tosylimidazol-5-ylmethyl ketone,
difluoromethyl 2-isopropyl-1-tosylimidazol-5-ylmethyl ketone, and
2-fluoro-1-tosylimidazol-5-ylmethyl difluoromethyl ketone.

EXAMPLE 13

When in the procedure of Example 8 an appropriate amount of the imidazole compounds obtained in Example 10 is substituted for 5-acetoxymethyl-1-tosylimidazole the following respective compounds are obtained:
2-fluoro-1-tosylimidazol-5-ylmethyl trifluoromethyl ketone,
2,4-dimethyl-1-tosylimidazol-5-ylmethyl trifluoromethyl ketone,
2,4-diisopropyl-1-tosylimidazol-5-ylmethyl trifluoromethyl ketone,
2-isopropyl-1-tosylimidazol-5-ylmethyl trifluoromethyl ketone, and
2-fluoro-1-tosylimidazol-5-ylmethyl trifluoromethyl ketone.

EXAMPLE 14

When in the procedure of Example 9 an appropriate amount of 2-fluoroimidazol-5-ylmethanol, 2,4-dimethylimidazol-5-ylmethanol, 2,4-diisopropylimidazol-5-ylmethanol, 2-isopropyl-4-ethylimidazol-5-ylmethanol or 2-fluoroimidazol-5-ylmethanol is substituted for 3-isopropylimidazol-5-ylmethanol the following respective ketone derivatives are obtained:
2-fluoro-1-tosylimidazol-5-ylmethyl fluoromethyl ketone,
2,4-dimethyl-1-tosylimidazol-5-ylmethyl fluoromethyl ketone,
2,4-diisopropyl-1-tosylimidazol-5-ylmethyl fluoromethyl ketone,
2-isopropyl-4-ethyl-1-tosylimidazol-5-ylmethyl fluoromethyl ketone, and
2-fluoro-1-tosylimidazol-5-ylmethyl fluoromethyl ketone.

EXAMPLE 15

When in the procedure of Example 5 (B) an appropriate amount of the ketone compounds obtained in Examples 12, 13 and 14 is substituted for 1-tosyl-5-imidazolylmethyl fluoromethyl ketone the following respective compounds are obtained:
2-(2-fluoroimidazol-5-yl)-1-difluoromethyl ethylamine hydrobromide,
1-difluoromethyl-2-(2,4-dimethylimidazol-5-yl)ethylamine hydrobromide,
1-difluoromethyl-2-(2,4-diisopropylimidazol-5-yl)ethylamine hydrobromide,
1-difluoromethyl-2-(2-isopropylimidazol-5-yl)ethylamine hydrobromide,
2-(2-fluoroimidazol-5-yl)-1-difluoromethylethylamine hydrobromide,
2-(2-fluoroimidazol-5-yl)-1-trifluoromethylethylamine hydrobromide,
2-(2,4-dimethylimidazol-5-yl)-1-trifluoromethylethylamine hydrobromide,
2-(2,4-diisopropylimidazol-5-yl)-1-trifluoromethylethylamine hydrobromide,
2-(2-isopropylimidazol-5-yl)-1-trifluoromethylethylamine hydrobromide,
2-(2-fluoroimidazol-5-yl)-1-trifluoromethylethylamine hydrobromide,
1-fluoromethyl-2-(2-fluoroimidazol-5-yl)ethylamine hydrobromide,
1-fluoromethyl-2-(2,4-dimethylimidazol-5-yl)ethylamine hydrobromide,
1-fluoromethyl-2-(2,4-diisopropylimidazol-5-yl)ethylamine hydrobromide,
1-fluoromethyl-2-(2-isopropyl-4-ethylimidazol-5-yl)ethylamine hydrobromide, and
1-fluoromethyl-2-(2-fluoroimidazol-5-yl)ethylamine hydrobromide.

EXAMPLE 16

N-[1-Fluoromethyl-2-(5-imidazolyl)ethyl]acetamide

A solution of 10 mmole of 1-fluoromethyl-2-(5-imidazolyl)ethylamine hydrobromide in 26 ml of 2 M sodium hydroxide solution is cooled to 5° C. To this solution is added simultaneously from 2 syringes 13 mmole of acetyl chloride and 5 ml of 2 M sodium hydroxide solution dropwise. After 2 hours the solution is neutralized by the addition of 16 ml of 1 M hydrochloric acid then evaporated to dryness. The residue is triturated with dichloromethane, filtered and evaporated to afford N-(1-difluoromethyl-2-(5-imidazolyl)ethyl]acetamide which is recrystallized from ethyl acetate.

When in the above procedure an appropriate amount of benzyl chloroformate is substituted for acetyl chloride, benzyl N-[1-fluoromethyl-2-(5-imidazolyl)ethyl]-carbamate is obtained.

EXAMPLE 17

N-[1-Fluoromethyl-2-[5-imidazolyl]ethyl]-2-aminopropionamide

To a solution of 10 mmole of benzyl N-[1-fluoromethyl-2-(5-imidazolyl)ethyl]carbamate in 20 ml of methylene chloride containing 1.1 g of triethylamine is added 10 mmole of benzyl chloroformate. After 2 hours at 25° C. the solution is washed with water and 1 N hydrochloric acid then evaporated to afford the dicarbobenzoxy derivative. To this residue is added 30 ml of 100% (w/w) hydrogen bromide in dioxane and the mixture is allowed to stand at 25° C. for 30 minutes after which 150 ml of ether is added. The resulting precipitate is filtered off and added to cold bicarbonate solution then rapidly extracted with dichloromethane. The dried organic phase is concentrated to afford 1-carbobenzoxy-5-[2-fluoromethyl-2-aminoethyl]imidazole which is treated in 10 ml of dichloromethane with 1.6 g (7 mmole) of N-carbobenzoxy alanine and 1.45 g (7 mmole) of N,N-dicyclohexylcarbodiimide for about 16 hours at 25° C. The mixture is then cooled to 0° C. and filtered. The organic solution is washed with 1 N hydrochloric acid and bicarbonate solution then dried and concentrated. The residue is treated with 30 ml of 100% (w/w) hydrogen bromide in dioxane for 30 minutes at 25° C. Addition of 150 ml of ether results in a precipitate of the hydrobromide which is filtered off and treated for about 16 hours with 50 ml of 1 N sodium hydroxide at 25° C. The resulting solution is adjusted to neutral pH and the product isolated from an Amberlite 120 H+ resin by elution with 2 M ammonia to yield N-[1-fluoromethyl-2-(5-imidazolyl)ethyl]-2-aminopropionamide.

We claim:
1. A compound of the formula

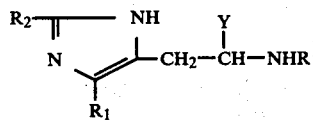

wherein Y is $FCH_2-$, $F_2CH-$, or $F_3C-$; R is hydrogen, alkylcarbonyl wherein the alkyl moiety has from 1 to 4 carbon atoms and is straight or branched, alkoxycarbonyl wherein the alkoxy moiety has from 1 to 4 carbon atoms and is straight or branched or

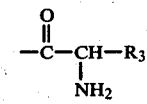

wherein $R_3$ is hydrogen, a straight or branched lower alkyl group of from 1 to 4 carbon atoms, benzyl or p-hydroxybenzyl; each of $R_1$ and $R_2$ is hydrogen, a straight or branched lower alkyl group of from 1 to 4 carbon atoms and may be the same or different, or $R_1$ is hydrogen and $R_2$ is fluorine; and pharmaceutically acceptable salts and individual optical isomers thereof.

2. A compound of claim 1 wherein R is hydrogen or alkylcarbonyl wherein the alkyl moiety has from 1 to 4 carbon atoms and is straight or branched.

3. A compound of claim 1 wherein R is hydrogen.

4. A compound of claim 1 wherein each of $R_1$ and $R_2$ is hydrogen or methyl.

5. A compound of claim 1 wherein each of $R_1$ and $R_2$ is hydrogen.

6. A compound of claim 1 wherein Y is $FCH_2-$ or $F_2CH-$.

7. A compound of claim 6 wherein each of R, $R_1$ and $R_2$ is hydrogen.

8. A compound of claim 1 which is 1-fluoromethyl-2-(5-imidazolyl)ethylamine or a pharmaceutically acceptable salt thereof.

9. A compound of claim 1 which is 1-difluoromethyl-2-(5-imidazolyl)ethylamine or a pharmaceutically acceptable salt thereof.

10. A compound of claim 1 which is 1-trifluoromethyl-2-(5-imidazolyl)ethylamine or a pharmaceutically acceptable salt thereof.

* * * * *

Notice of Adverse Decision in Interference

In Interference No. 100,906, involving Patent No. 4,221,914, P. Bey and M. Jung, ALPHA-HALOMETHYL DERIVATIVES OF HISTAMINE AND RELATED COMPOUNDS, final judgment adverse to the patentees was rendered Jan. 27, 1983, as to claim 8.

[*Official Gazette November 8, 1983.*]